United States Patent
Hernández et al.

(10) Patent No.: US 10,548,614 B2
(45) Date of Patent: Feb. 4, 2020

(54) TRICUSPID VALVE REPAIR SYSTEM

(71) Applicant: Evalve, Inc., Santa Clara, CA (US)

(72) Inventors: Carlos G. Hernández, San Francisco, CA (US); Laura M. Kalvass, Mountain View, CA (US); Scott C. Mosher, San Francisco, CA (US); Santosh V. Prabhu, Sunnyvale, CA (US); Paolo Romitelli, Tivoli (IT); Lauren G. Troxler, San Francisco, CA (US); Dylan T. Van Hoven, San Carlos, CA (US)

(73) Assignee: Evalve, Inc., Santa Clara, CA (US)

( * ) Notice: Subject to any disclaimer, the term of this patent is extended or adjusted under 35 U.S.C. 154(b) by 370 days.

(21) Appl. No.: 15/364,054

(22) Filed: Nov. 29, 2016

(65) Prior Publication Data

US 2018/0146966 A1    May 31, 2018

(51) Int. Cl.
*A61B 17/122* (2006.01)
*A61B 17/128* (2006.01)
(Continued)

(52) U.S. Cl.
CPC .... *A61B 17/1285* (2013.01); *A61B 17/00234* (2013.01); *A61B 17/122* (2013.01);
(Continued)

(58) Field of Classification Search
CPC .......... A61B 17/1285; A61B 17/00234; A61B 17/122; A61B 17/1227; A61B 17/1327;
(Continued)

(56) References Cited

U.S. PATENT DOCUMENTS 5,171,259 A    12/1992  Inoue
5,607,445 A     3/1997  Summers
(Continued)

FOREIGN PATENT DOCUMENTS

WO    WO 91/15155 A1    10/1991
WO    WO 2004/069055 A2   8/2004
(Continued)

OTHER PUBLICATIONS

International Search Report dated Jan. 29, 2018 in International Application No. PCT/US2017/062734, European Patent Office, pp. 1-4.
(Continued)

*Primary Examiner* — Erich G Herbermann
(74) *Attorney, Agent, or Firm* — Baker Botts L.L.P.

(57) ABSTRACT

Devices and methods for use in a cardiac valve repair procedure, particularly a tricuspid valve repair procedure. An interventional clip device includes a pair of distal elements rotatably joined to a coupling member, and a pair of proximal elements resiliently biased toward the distal elements to grasp tissue therebetween. The proximal elements include a plurality of adjustable tines moveable between a retracted configuration and an open configuration to avoid damage to tissue prior to engagement while allowing tines to enhance gripping to targeted tissue when open. A delivery system enables delivery of an interventional clip to a targeted cardiac valve, and includes a support structure for maintaining position relative to the cardiac valve.

6 Claims, 10 Drawing Sheets

(51) Int. Cl.
*A61B 17/00* (2006.01)
*A61F 2/24* (2006.01)
*A61B 17/28* (2006.01)
*A61B 17/29* (2006.01)

(52) U.S. Cl.
CPC ........ *A61B 17/1227* (2013.01); *A61F 2/2463* (2013.01); *A61F 2/2466* (2013.01); *A61B 2017/00243* (2013.01); *A61B 2017/00783* (2013.01); *A61B 2017/00862* (2013.01); *A61B 2017/00867* (2013.01); *A61B 2017/2825* (2013.01); *A61B 2017/2926* (2013.01)

(58) Field of Classification Search
CPC ........ A61B 17/128; A61B 2017/00783; A61B 2017/00862; A61B 2017/00867; A61B 2017/2825; A61B 2017/2926; A61B 2017/00243; A61F 2/2463; A61F 2/2466; A61F 2/2475
See application file for complete search history.

(56) References Cited

U.S. PATENT DOCUMENTS

| | | | |
|---|---|---|---|
| 5,924,424 | A | 7/1999 | Stevens et al. |
| 6,129,758 | A | 10/2000 | Love |
| 7,112,207 | B2 | 9/2006 | Allen et al. |
| 7,563,267 | B2 * | 7/2009 | Goldfarb ........... A61M 25/0136 606/151 |
| 7,563,273 | B2 | 7/2009 | Goldfarb et al. |
| 7,569,062 | B1 | 8/2009 | Kuehn et al. |
| 7,666,204 | B2 | 2/2010 | Thornton et al. |
| 8,470,028 | B2 | 6/2013 | Thornton et al. |
| 8,753,362 | B2 | 6/2014 | Widomski et al. |
| 9,180,005 | B1 | 11/2015 | Lashinski et al. |
| 9,750,505 | B2 | 9/2017 | Miles et al. |
| 9,770,232 | B2 | 9/2017 | Amin et al. |
| 2002/0013571 | A1 | 1/2002 | Goldfarb et al. |
| 2003/0018358 | A1 | 1/2003 | Saadat |
| 2003/0139819 | A1 | 7/2003 | Beer et al. |
| 2004/0073242 | A1 | 4/2004 | Chanduszko |
| 2004/0176799 | A1 | 9/2004 | Chanduszko et al. |
| 2004/0220610 | A1 | 11/2004 | Kreidler et al. |
| 2005/0043759 | A1 | 2/2005 | Chanduszko |
| 2005/0065548 | A1 | 3/2005 | Marino et al. |
| 2005/0273135 | A1 | 12/2005 | Chanduszko et al. |
| 2005/0288786 | A1 | 12/2005 | Chanduszko |
| 2006/0122646 | A1 | 6/2006 | Corcoran et al. |
| 2006/0265004 | A1 | 11/2006 | Callaghan et al. |
| 2006/0271089 | A1 | 11/2006 | Alejandro et al. |
| 2007/0010851 | A1 | 1/2007 | Chanduszko |
| 2007/0027533 | A1 * | 2/2007 | Douk ................. A61F 2/2445 623/2.11 |
| 2007/0073337 | A1 | 3/2007 | Abbott et al. |
| 2007/0112380 | A1 | 5/2007 | Figulla et al. |
| 2007/0167981 | A1 | 7/2007 | Opolski et al. |
| 2007/0179527 | A1 | 8/2007 | Eskuri et al. |
| 2007/0250081 | A1 | 10/2007 | Cahill et al. |
| 2007/0260305 | A1 | 11/2007 | Drews et al. |
| 2009/0188964 | A1 | 7/2009 | Orlov |
| 2010/0004740 | A1 | 1/2010 | Seguin et al. |
| 2010/0234878 | A1 | 9/2010 | Hruska et al. |
| 2010/0234885 | A1 | 9/2010 | Frazier et al. |
| 2011/0060407 | A1 | 3/2011 | Ketai et al. |
| 2011/0276086 | A1 | 11/2011 | Al-Qbandi et al. |
| 2013/0066341 | A1 | 3/2013 | Ketai et al. |
| 2013/0282110 | A1 | 10/2013 | Schweich, Jr. et al. |
| 2013/0289718 | A1 * | 10/2013 | Tsukashima ......... A61F 2/2448 623/2.11 |
| 2014/0005778 | A1 | 1/2014 | Buchbinder et al. |
| 2014/0163669 | A1 | 6/2014 | Ben-zvi et al. |
| 2014/0200662 | A1 | 7/2014 | Eftel et al. |
| 2015/0066077 | A1 | 3/2015 | Akpinar |
| 2015/0173765 | A1 | 6/2015 | Miller et al. |
| 2016/0022417 | A1 | 1/2016 | Karapetian et al. |
| 2016/0030169 | A1 | 2/2016 | Shahriari |
| 2018/0055633 | A1 | 3/2018 | Costello et al. |

FOREIGN PATENT DOCUMENTS

| | | |
|---|---|---|
| WO | WO 2004/069055 A3 | 8/2004 |
| WO | WO 2014/018907 A1 | 1/2014 |
| WO | WO 2014/182849 A1 | 11/2014 |

OTHER PUBLICATIONS

International Search Report dated Jun. 12, 2018 in International Application No. PCT/US2018/019033.

International Search Report dated Oct. 13, 2017 from International Application No. PCT/US2017/039811, European Patent Office ISA/EP.

Vismara et al., "Transcatheter Edge-to-Edge Treatment of Functional Tricuspid Regurgitation in an Ex Vivo Pulsatile Heart Model," JACC 68(10):1024-1033 (2016).

* cited by examiner

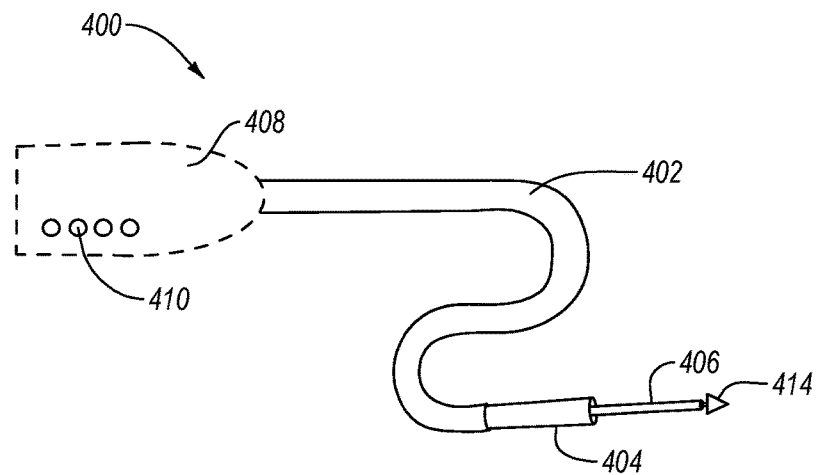
FIG. 11A
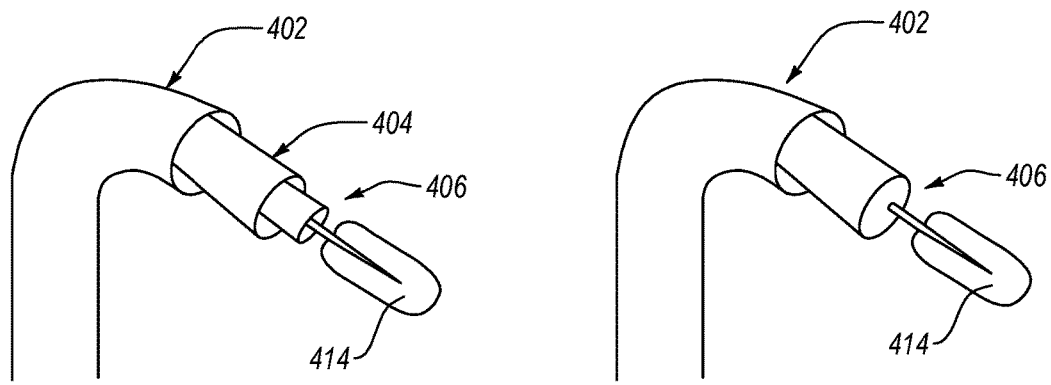
FIG. 11B
FIG. 11C

TRICUSPID VALVE REPAIR SYSTEM

BACKGROUND

The tricuspid valve controls blood flow from the right atrium to the right ventricle of the heart, preventing blood from flowing backwards from the right ventricle into the right atrium so that it is instead forced through the pulmonary valve and into the pulmonary arteries for delivery to the lungs. A properly functioning tricuspid valve opens and closes to enable blood flow in one direction. However, in some circumstances the tricuspid valve is unable to close properly, allowing blood to regurgitate back into the atrium. Such regurgitation can result in shortness of breath, fatigue, heart arrhythmias, and even heart failure.

Tricuspid valve regurgitation has several causes. Functional tricuspid valve regurgitation (FTR) is characterized by structurally normal tricuspid valve leaflets that are nevertheless unable to properly coapt with one another to close properly due to other structural deformations of surrounding heart structures. Often, the right ventricle is dilated as a result of pulmonary hypertension or an abnormal heart muscle condition (cardiomyopathy).

Other causes of tricuspid valve regurgitation are related to degenerative valves and/or defects of the tricuspid valve leaflets, tricuspid valve annulus, or other tricuspid valve structures. In some circumstances, tricuspid valve regurgitation is a result of infective endocarditis, blunt chest trauma, rheumatic fever, Marfan syndrome, carcinoid syndrome, improper placement of pacemaker leads, or congenital defects to the structure of the heart.

Tricuspid valve conditions are also often associated with problems related to the left side of the heart, such as mitral valve regurgitation. In particular, FTR is often associated with left heart pathologies, though it is typically left untreated during left heart surgeries. Left heart pathologies such as mitral valve regurgitation and stenosis can induce pressure and volume overload in the right ventricle, which in turn can induce ventricle enlargement and tricuspid annular dilation. Though often relatively mild at the time of treatment of the left heart, this annular dilation of the tricuspid valve is progressive and asymmetric, and FTR becomes more severe as time goes on. Reoperation for repair of the tricuspid valve is often needed owing to the degenerative character of the pathology.

Tricuspid valve regurgitation is often treated by replacing the tricuspid valve with a replacement valve implant. However, valve replacement procedures typically involve drastic measures that remove or render inoperable the natural tricuspid valve tissues. Moreover, some patients are not suitable candidates for a valve replacement procedure. For example, patients having pacemaker leads in the vicinity of the valve cannot easily or safely undergo a valve replacement procedure.

Other treatment options involve repairing the valve through an interventional procedure. However, issues can arise related to deployment and effectiveness of various treatment options. For instance, properly positioning and aligning a repair device with respect to the tricuspid valve can be difficult, particularly considering that the valve leaflets and other structures are continuously moving within the dynamic cardiac environment.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices and methods for repairing tissue, such as tissue of a malfunctioning cardiac valve, including a regurgitant tricuspid valve. In some embodiments, an interventional device is configured as a clip device. The clip device includes a pair of distal elements rotatably joined to a coupling member, and a pair of proximal elements resiliently biased toward the distal elements. The distal elements are configured to receive the proximal elements so as to enable the grasping of tissue therebetween. The proximal elements include a plurality of adjustable tines moveable between a retracted configuration and an open configuration. In the open configuration, the tines are positioned more perpendicular to the respective longitudinal axes of the proximal elements so as to enable enhanced grasping of tissue by the proximal elements.

Certain embodiments are directed to the arrangement and attachment of one or more clip devices and related techniques to repair a malfunctioning cardiac valve, such as, for example, a regurgitant tricuspid valve.

Certain embodiments are directed toward delivery devices for delivering an interventional device to a targeted treatment area within the body. A delivery device includes a guide catheter having a proximal end and a distal end, the guide catheter being configured to transmit an interventional device to a targeted area. The guide catheter has a supportable section and a distal section defined as the section more distal from the supportable section. The delivery device also includes an adjustable support structure disposed at the support section. The adjustable support structure is configured to expand upon deployment so as to support the guide catheter against adjacent anatomy and to support a desired orientation of the distal section of the guide catheter with respect to a targeted anatomical site.

For example, in a tricuspid repair procedure where the guide catheter is routed to the right atrium of the heart, the support structure can be positioned on the guide catheter so as to be within the inferior vena cava (e.g., in transfemoral approach applications), or superior vena cava (e.g., in transjugular approach applications) when the guide catheter is properly positioned to deliver an interventional device (e.g., an interventional tissue clip) to the tricuspid valve. The support structure can then deploy to abut against the walls of the vena cava to support the position/orientation of the distal section of the guide catheter.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 11A-11D illustrate a delivery device configured for delivering an interventional clip to a targeted treatment site;

DETAILED DESCRIPTION

At least some of the embodiments described herein are directed to devices and methods for repairing a malfunctioning cardiac valve, such as a regurgitant tricuspid valve. Although many of the examples illustrated and described herein are directed to tricuspid valve regurgitation, it will be understood that the principles, features, and components described herein may also be applied in other applications, such as repair of other heart valves, or use in other interventional procedures or treatment applications.

Figure 1:
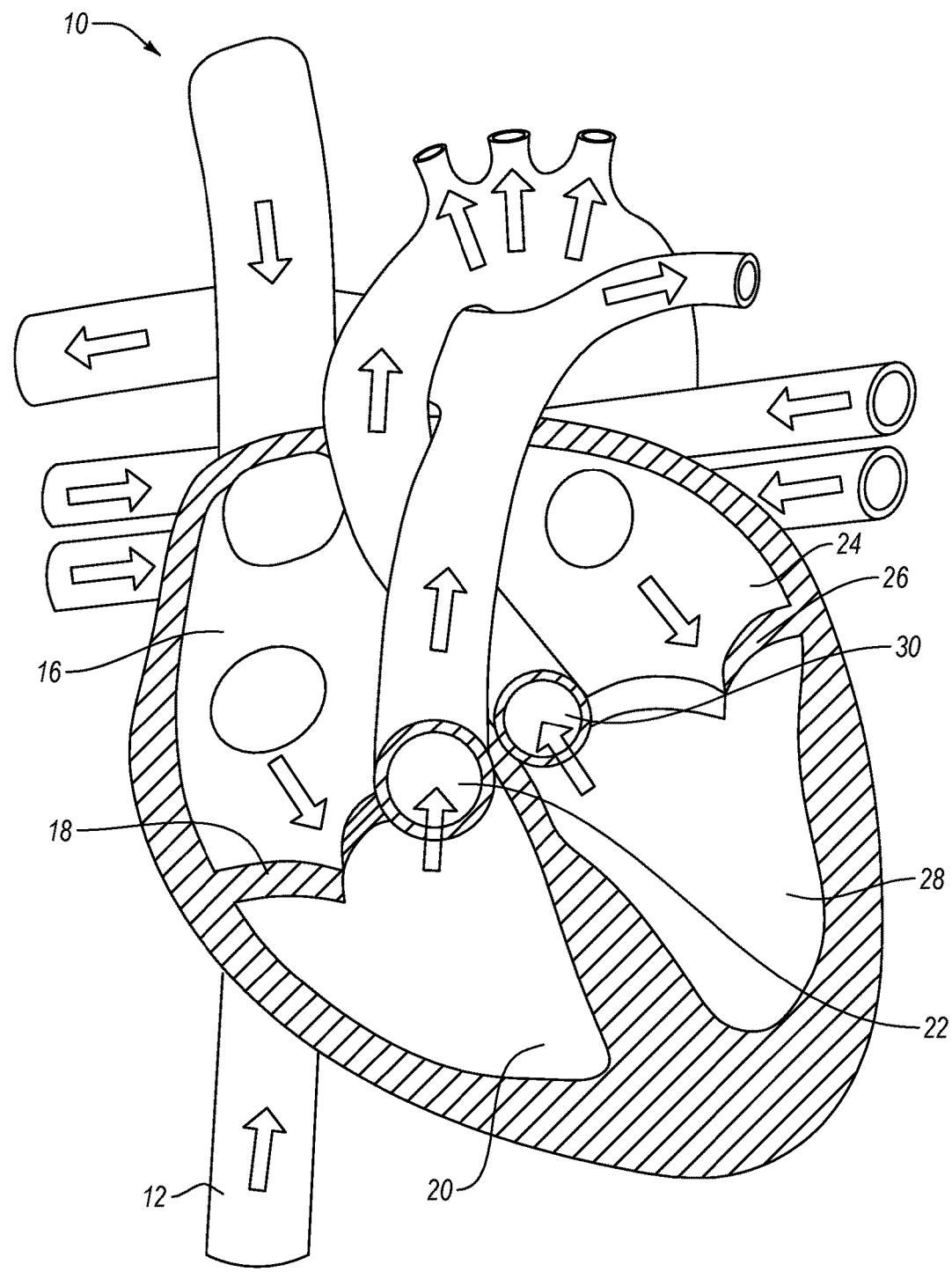
FIG. 1 illustrates a human heart showing normal blood flow paths.

FIG. 1 illustrates a cross-sectional view of a heart 10 showing a normal blood flow path through the heart. Deoxygenated blood enters the right atrium 16 through the superior vena cava 14 and superior vena cava 12. During diastole, suction from expansion of the right ventricle 20 and pressure from contraction of the right atrium 16 forces blood from the right atrium 16 across the tricuspid valve 18 and into the right ventricle 20. During ventricular systole, blood is then forced from the right ventricle 20 through the pulmonary valve 22 and into the pulmonary arteries for delivery to the lungs. In a normally functioning heart, the tricuspid valve 18 closes during systole to prevent backwards movement of blood from the right ventricle 20 back into the right atrium 16. When a tricuspid valve is not functioning properly, it may fail to fully close such that some of the blood passes back across the tricuspid valve 18 and into the right atrium 16, rather than through the pulmonary valve 22.

Oxygenated blood returning from the lungs enters the left atrium 24, where it is then passed through the mitral valve 26 and into the left ventricle 28. During ventricular systole, the blood is then passed from the left ventricle through the aortic valve for delivery throughout the body. Similar to the right side of the heart, failure of the mitral valve 26 to fully close during ventricular systole leads to regurgitation of blood from the left ventricle 28 back into the left atrium 24. In some circumstances, problems related to mitral valve regurgitation or other issues with the left side of the heart also cause or are associated with structural issues on the right side of the heart, such as tricuspid valve regurgitation.

Figure 2:
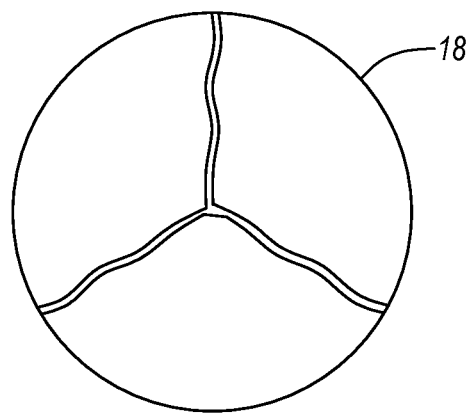
FIG. 2 illustrates a superior view of a normally functioning tricuspid valve in a closed position.
Figure 3:
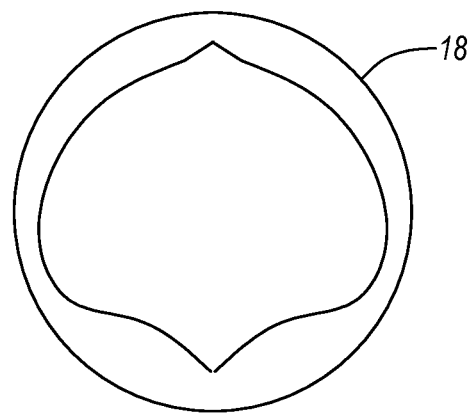
FIG. 3 illustrates a superior view of a tricuspid valve in an open position.
Figure 4:
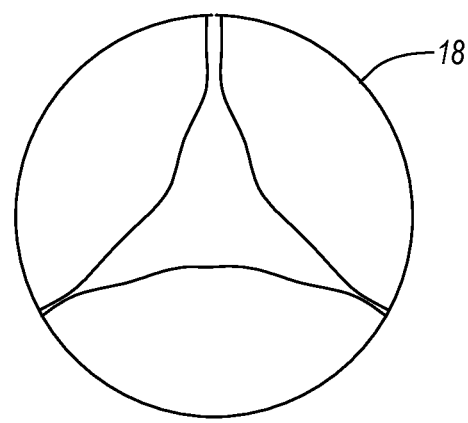
FIG. 4 illustrates a superior view of a malfunctioning tricuspid valve unable to properly close.

FIGS. 2-4 illustrate superior views of a tricuspid valve 18 in various states and positions. FIG. 2 illustrates a properly functioning tricuspid valve 18 in a closed position. A properly functioning tricuspid valve 18 takes this form during ventricular systole in order to block backflow of blood. As shown, when in the closed position, the three leaflets of the tricuspid valve 18 coapt to fully close the valve. FIG. 3 illustrates a properly functioning tricuspid valve 18 in an open position. When open, the leaflets of the tricuspid valve 18 extend downward into the right ventricle so that passage of blood through the tricuspid valve 18 is provided.

FIG. 4 illustrates a defective tricuspid valve 18 during ventricular systole. In contrast to the properly closed tricuspid valve of FIG. 2, the leaflets of the defective tricuspid valve are unable to fully coapt, leaving a passage through which regurgitant blood may pass. The inability to fully close may be due to defects to the leaflets themselves, or to defects to other structures of the heart which deform the tricuspid valve annulus or stretch the chordae tendineae, for example.

Figure 5A:
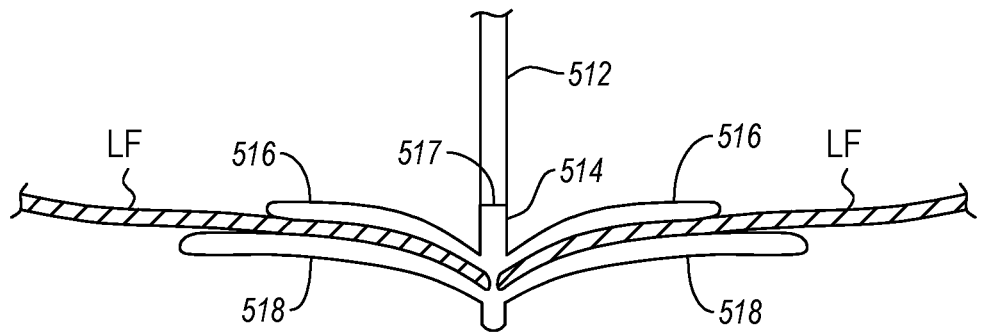
FIG. 5A-5C illustrate an embodiment of an interventional clip in various positions relative to targeted cardiac valve leaflets.
Figure 5B:
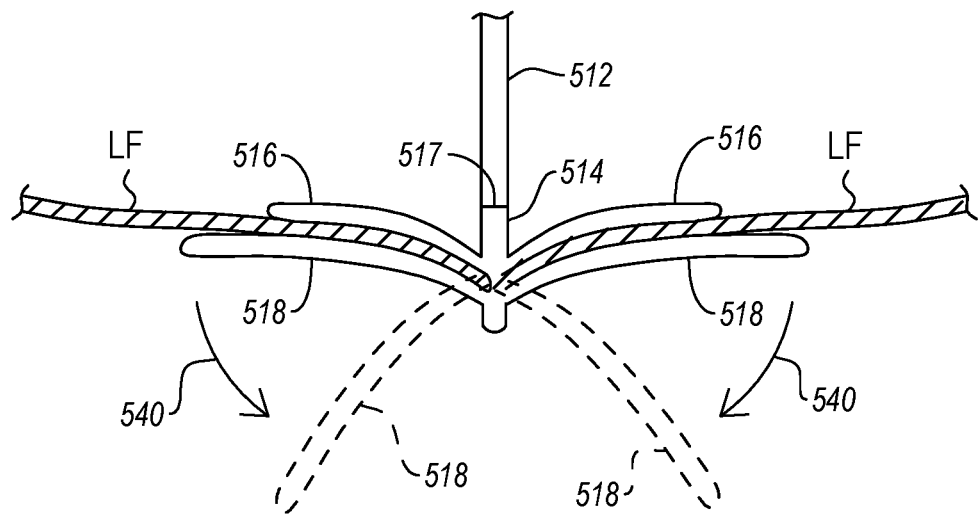
Figure 5C:
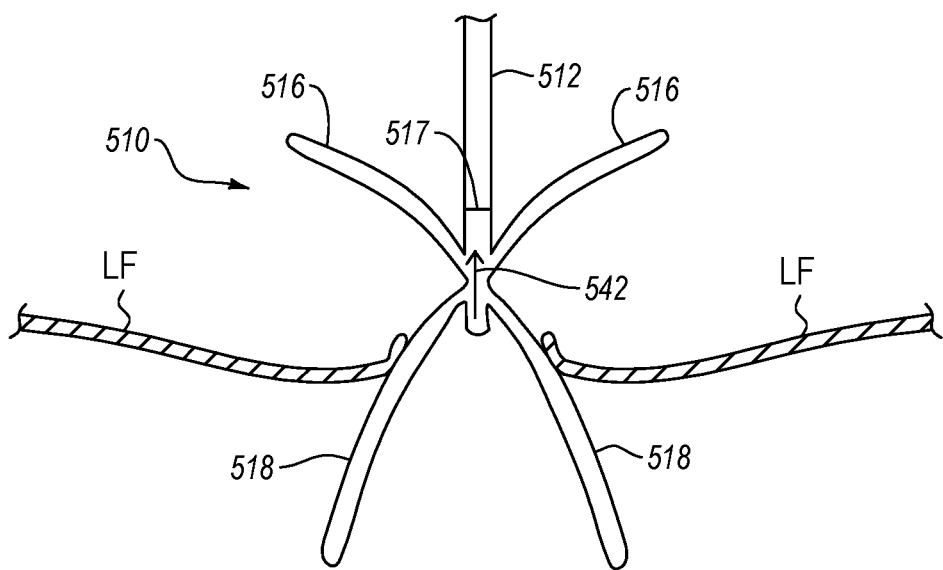

FIGS. 5A-5C illustrate an exemplary interventional device 510 that may be utilized in one or more of the applications described herein. The illustrated device includes a shaft 512 and a repair device 514 (also referred to herein as a "clip"). The interventional device 510 is illustrated as having approached a pair of leaflets "LF" from the atrial side and grasped the leaflets.

The repair device 514 is releasably attached to the shaft 512 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the tricuspid valve, proximal shall refer to the atrial or upstream side of the valve leaflets and distal shall refer to the ventricular or downstream side of the valve leaflets.

The illustrated repair device 514 includes proximal elements 516 and distal elements 518 (each generally referred to herein as "gripping elements" or "arms"), which protrude radially outward and are positionable on opposite sides of the leaflets so as to capture or retain the leaflets therebetween. The proximal elements 516 are preferably comprised of cobalt chromium, nitinol, or stainless steel, and the distal elements 518 are preferably comprised of a cobalt chromium alloy (such as Elgiloy®) or stainless steel; however any suitable materials may be used. The repair device 514 is attachable to the shaft 512 by a coupling mechanism 517. The coupling mechanism 517 allows the repair device 514 to detach and be left behind as an implant to hold the leaflets together in the coapted position. The coupling mechanism 517 may be a mechanical linkage (e.g., including one or more of a threaded linkage, clasp, clip, pin, tab, receiver slot, or other mechanical fastening component), magnetic linkage, or other coupling means.

In some circumstances, it may be desired to reposition or remove the repair device 14 after the proximal elements 516, distal elements 518, or both have been deployed. Such repositioning or removal may be desired for a variety of reasons, such as to re-approach the valve in an attempt to achieve better valve function, more optimal positioning of the device 514 on the leaflets, better purchase on the leaflets, to detangle the device 514 from surrounding tissue such as chordae, to exchange the device 514 with one having a different design, or to abort the fixation procedure, for example. To facilitate repositioning or removal of the repair device 514 the distal elements 518 are releasable and optionally invertible to a configuration suitable for withdrawal of the device 514 from the valve without tangling or interfering with or damaging the chordae, leaflets, or other tissue.

FIG. 5B illustrates an inversion configuration wherein the distal elements 518 are moveable in the direction of arrows 540 to an inverted position. Likewise, the proximal elements 516 may be selectively raised. In the inverted configuration, the repair device 514 may be repositioned to a desired orientation and then the distal elements may be reverted to a deployed/grasping position against the leaflets as shown in FIG. 5A. Alternatively, the repair device 514 may be withdrawn from the leaflets as shown by the arrow 542 in FIG. 5C.

The inverted configuration reduces trauma to the leaflets and minimizes any entanglement of the device with surrounding tissues. Once the device 514 has been withdrawn through the valve leaflets, the proximal and distal elements may be moved to a closed configuration suitable for removal from the body or for reinsertion through the tricuspid valve.

Figure 6:
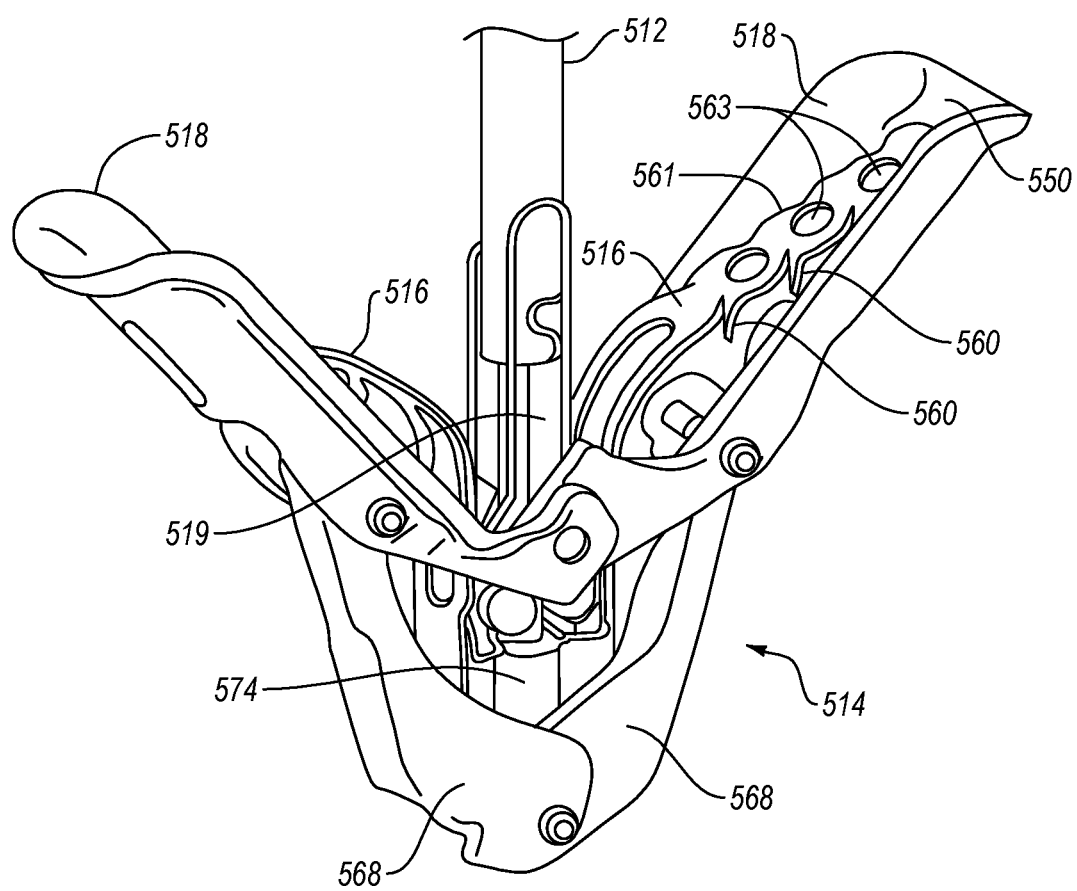
FIG. 6 illustrates a detailed view of the interventional clip of FIGS. 5A-5C.

FIG. 6 illustrates a detailed view of the repair device 514 (i.e., clip 514). The clip 514 includes a coupling member 519 and a pair of opposed distal elements 518, the distal elements 518 being formed as elongate arms rotatably connected to the coupling member 519. The engagement surfaces 550 of the distal elements 518 have a cupped or concave shape to surface area in contact with tissue and to assist in grasping and holding valve leaflets when deployed.

When deployed, valve leaflets are grasped between the distal elements 518 and a set of proximal elements 516, which are resiliently cantilevered from coupling member 519. The proximal elements 516 are resiliently biased toward the distal elements 518. Each of the proximal elements 516 is shaped and positioned to be at least partially recessed within the concavity of the corresponding distal element 518 when no tissue is present. The proximal elements 16 include a plurality of openings 563 and scalloped side edges 561 to increase grip on tissue. The proximal elements 516 may include additional or alternative frictional accessories, frictional features, or grip-enhancing elements to assist in grasping and/or holding the leaflets. In preferred embodiments, the frictional accessories comprise tines 560 having tapering pointed tips extending toward engagement surfaces 550. Additionally, or alternatively, other frictional accessories may be used, such as barbs, prongs, windings, bands, barbs, grooves, channels, bumps, surface roughening, sintering, high-friction pads, coverings, coatings, or a combination of these.

The clip 514 also includes an actuation mechanism formed from two linking legs 568 each rotatably joined with one of the distal elements 518 and rotatably joined at an opposite end to a stud 574. As the stud 574 is moved axially, the legs 568 are rotated, which also causes rotation of the distal elements 518 between closed, open, and inverted positions. Likewise, immobilization of the stud 574 holds the legs 568 in place to lock the distal elements 518 in a desired position.

In the open position, the clip 514 can engage the tissue to be approximated. During deployment in a tricuspid valve repair procedure, the distal elements 518 are oriented to be perpendicular to the line of coaptation, and are then positioned so that the engagement surfaces 550 contact the ventricular surface of the valve leaflets. The proximal elements 516 remain on the atrial side of the valve leaflets so that the leaflets may be grasped between the proximal elements 516 and distal elements 518. Once the clip 514 has been properly positioned, the proximal elements 516 are lowered toward the engagement surfaces 550 (e.g., by releasing tension on attached control lines or through another deployment mechanism) so that the leaflets are held therebetween.

After the leaflets have been captured between the proximal elements 516 and distal elements 518 in a desired arrangement, the distal elements 518 may be rotatably moved toward a closed position, and the clip 514 may be decoupled from the shaft 512 and/or any other delivery mechanisms. Embodiments of tissue fixation clips are further described in U.S. Pat. No. 7,666,204, which is incorporated herein by this reference in its entirety.

FIGS. 7A to 7D illustrate superior views of a tricuspid valve showing various embodiments of tricuspid repair procedures that may be performed in accordance with the description herein. In the Figures, "S" indicates the septal leaflet, "A" indicates the anterior leaflet, and "P" indicates the posterior leaflet. Although the following exemplary embodiments may show particular placement of one or more clips relative to the illustrated leaflets, it will be understood that the same principles may be applied to the other leaflets as desired and/or as dictated by application-specific contexts.

Figure 7A:
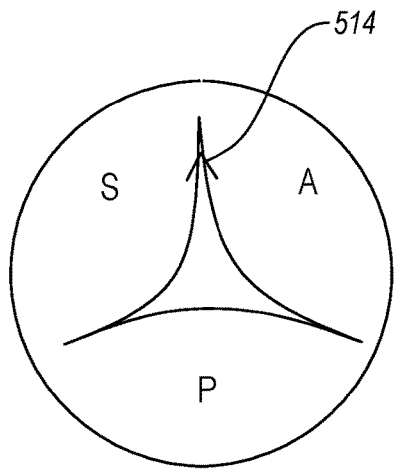
FIGS. 7A-7D illustrate various embodiments of tricuspid valve repair methods, showing different clip placement variations.

As shown in FIG. 7A, a clip 514 may be deployed between two of the leaflets of a tricuspid valve so as to provide for improved coaptation between the two leaflets. The clip 514 is shown positioned between the S-A line of coaptation. One or more clips may additionally or alternatively be deployed at other lines of coaptation (the S-P line of coaptation or the A-P line of coaptation). In some circumstances, the deployment of a single clip 514 can provide sufficient reduction or elimination of regurgitation. For example, in circumstances in which only a single line of coaptation shows any substantial pathology, placement of a clip 514 at that particular line of coaptation may provide sufficient structural effects for treating the regurgitant valve.

The clip 514 can be deployed at a commissural position of the line of coaptation, or at a medial position along the line of coaptation. As used herein, "commissural placement" and similar terms refer to clip placement that is substantially near a commissure of two of the tricuspid valve leaflets, for example, within about 5 mm or less of the commissure, or within approximately ⅓ of the length of the line of coaptation between the two tricuspid valve leaflets nearest to the commissure, or close enough to the commissure that a second clip of similar size and shape cannot be placed between the annulus and the initial clip. As used herein, "medial placement" and similar terms refer to clip placement at a location along the line of coaptation that is relatively farther from the respective commissure, such as more than about 5 mm, or approximately ½ the length of the line of coaptation between the two tricuspid leaflets associated with the respective commissure, or placement such that a double orifice is created after initial clip placement.

Figure 7B:
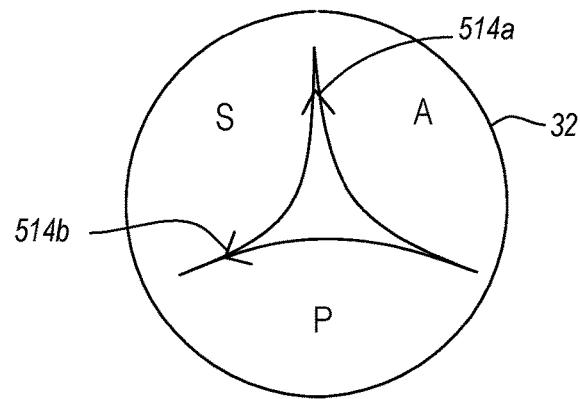

FIG. 7B illustrates another embodiment in which two independent clips 514a and 514b are deployed in some combination at the tricuspid valve. For example, in the illustrated embodiment, a first clip 514a is positioned at the S-A position and a second clip 514b is positioned at the S-P position. In other implementations, one of the deployed clips may be alternatively positioned at the A-P position. In the illustrated embodiment, each of the deployed clips 514a and 514b are shown deployed at a medial portion of the respective line of coaptation (i.e., radially inwards from the annulus 32 of the tricuspid valve). In alternative implementations, one or more of the clips may be deployed at a commissural position (i.e., at or nearer to the section where two leaflets meet near the valve annulus 32).

Figure 7C:
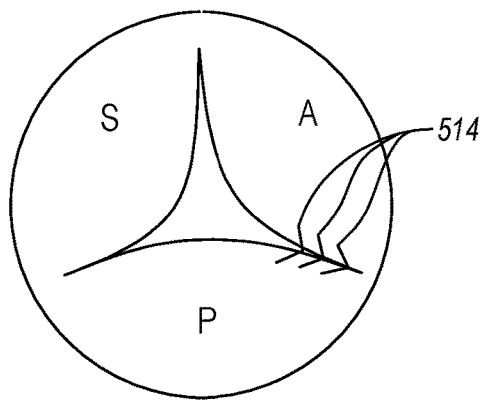

FIG. 7C illustrates another embodiment in which a plurality of clips 514 are deployed along the same line of coaptation in order to approximate or "zip" the adjacent leaflets together. In the illustrated embodiment, three clips 514 are positioned along the A-P line of coaptation so as to substantially fix the relative positioning of the posterior and anterior leaflets to one another in order to reduce or eliminate regurgitant flow through the tricuspid valve. Alternative embodiments may include a plurality of clips positioned at another line of coaptation.

Figure 7D:
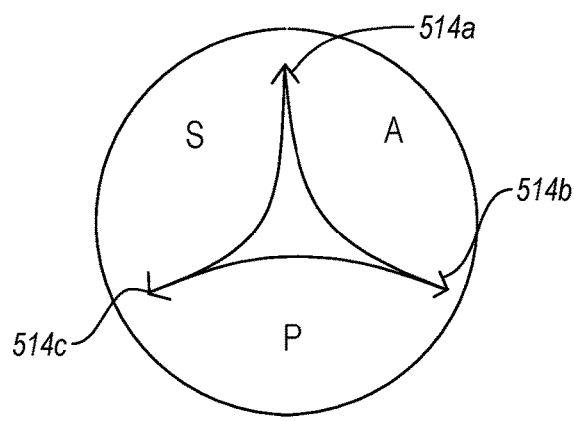

FIG. 7D illustrates another embodiment in which a plurality of clips 514a, 514b, and 514c are respectively positioned at or near each commissure location in order to provide the functional effect of a reduced tricuspid valve annulus. Alternatively, one or more of the clips 514a, 514b, and 514c may be omitted, or may be positioned a desired medial distance from the respective commissures in order to provide a desired level of functional annulus reduction.

The clip placement embodiments illustrated in FIGS. 7A-7D are exemplary only. Other embodiments include combinations of the illustrated clip placements and/or clips positioned at other locations of the tricuspid valve. For example, some embodiments may include a medially positioned clip on a first line of coaptation and a commissurally positioned clip on a second line of coaptation.

In preferred embodiments, at least one clip is positioned on a line of coaptation that includes the septal leaflet. Results have shown that clip placement on the S-A and/or S-P line of coaptation beneficially increases cardiac output and pulmonary pressure, relative to cardiac output and pulmonary pressure of the pathological condition prior to clip placement. Presently preferred single clip placement embodiments, which have been shown to provide beneficial treatment results, include S-A commissural placement, or even more preferably medial S-P placement or medial S-A placement. Presently preferred double clip placement embodiments, which have been shown to provide beneficial treatment results, include S-P medial with S-P commissural placement (zipper placement), S-P commissural with S-A commissural placement, A-P medial with S-P medial placement, and A-P medial with S-A medial placement. Even more preferred double clip placement embodiments include S-P medial with S-A medial placement, S-A commissural with S-A medial placement (zipper placement), S-A commissural with S-P medial placement, and S-A medial with S-P commissural placement.

Figure 8A:
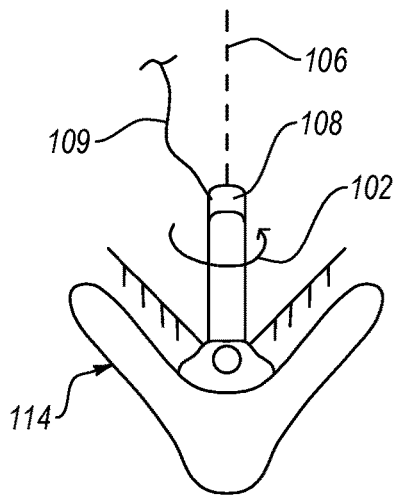
FIGS. 8A and 8B illustrate alternative embodiments of interventional clip devices, showing rotatable joint functionality and extended arm embodiments, respectively.

FIG. 8A illustrates an embodiment of an interventional clip 114 that may be utilized in one or more of the tricuspid repair embodiments described herein. The clip 114 may be configured similarly to the clip 14 shown in FIG. 6. As indicated by arrow 102, the clip 114 is also configured so as to be rotatable about a shaft axis 106. Such rotational control beneficially allows the clip 114 to be properly aligned with targeted tricuspid valve leaflets (e.g., so that clip arms are perpendicular to the targeted line of coaptation). The rotational functionality may be imparted by a rotational joint 108 which rotationally couples the clip 114 to a delivery catheter or other delivery structure (not shown; see FIGS. 11A and 11B). In some embodiments, the rotational joint 108 is configured as a set of one or more ball and socket joints, universal joints, other joints that impart axial rotation capabilities, or combinations thereof. In some embodiments, one or more control lines 109 extend proximally from the clip 114 to enable control of various functions of the clip 114. In the illustrated embodiment, one or more control lines 109 may be wrapped around or otherwise associated with the rotational joint 108 so that axial rotation of the clip 114 may be controlled by tensioning of the corresponding control line 109.

In alternative embodiments, a rotational joint is omitted, and rotational control is provided by enabling rotation of a delivery catheter (to which the clip 114 is attached) relative to one or more additional sleeves, catheters, or other guide structures within which the guide catheter is disposed (see FIGS. 11A and 11B). Such embodiments may include one or more friction-reducing components or features in order to limit binding of the guide catheter against the inner surface of the sleeve or other structure within which the guide catheter is disposed. For example, the outer surface of the guide catheter and/or inner surface of the sleeve may include a lubricious coating and/or may include one or more sections formed with a low friction material (e.g., nylon, polytetrafluoroethylene, etc.).

Figure 8B:
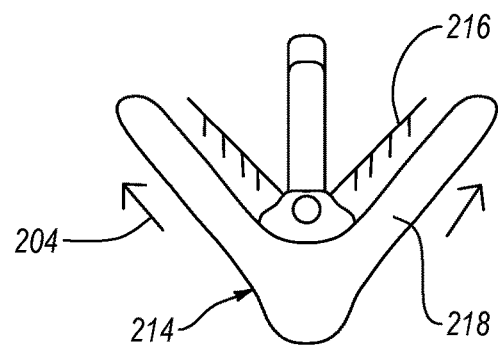

FIG. 8B illustrates another embodiment of an interventional clip 214 that may be utilized in one or more of the tricuspid repair embodiments described herein. The clip 114 may be configured similarly to the clip 14 shown in FIG. 6. The illustrated clip 214 also includes an extended arm configuration, as indicated by arrows 204. For example, the distal elements 218 and/or the proximal elements 216 may have an extended length that beneficially provides for improved grasping and fixing of tricuspid leaflet tissue. In contrast to a typical clip configuration (e.g., configured for a mitral valve repair procedure), the illustrated embodiment is particularly beneficial for grasping and fixing tissues in a tricuspid valve repair application. For example, a typical clip configuration includes distal elements and proximal elements with lengths of 6 to 8 mm. In the illustrated embodiment, the distal elements 218 and/or proximal elements 216 may have lengths greater than about 8 mm, greater than about 10 mm, greater than about 12 mm, or greater than about 15 mm, or may have lengths within a range defined by any two of the foregoing values.

Figure 9A:
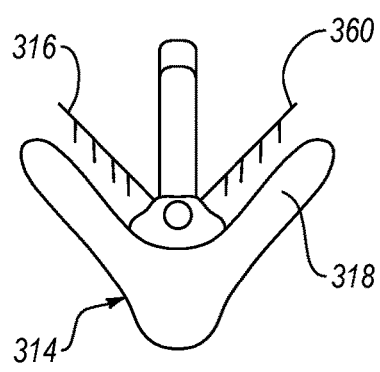
FIGS. 9A and 9B illustrate an embodiment of an interventional clip including a proximal element with adjustable tines selectively moveable between a retracted configuration and an open configuration for gripping tissue.
Figure 9B:
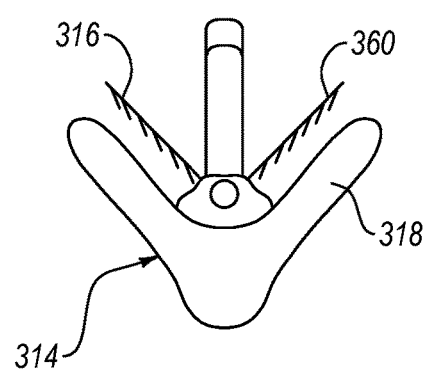

FIGS. 9A and 9B illustrate another embodiment of an interventional clip 314 that may be utilized in one or more of the tricuspid repair embodiments described herein. The illustrated embodiment includes one or more proximal elements 316 configured with adjustable tines 360. FIG. 9A illustrates the proximal element 316 with tines 360 in an extended configuration, and FIG. 9B illustrates the proximal element 316 with tines 360 in a retracted or closed configuration. The adjustable tines 360 can beneficially reduce the risk of undesirable tissue damage during deployment of the clip 314. For example, during deployment, as the distal elements 318 are positioned against one side of the tricuspid valve (e.g., the ventricular side), but before the proximal elements 316 are deployed to engage leaflet tissue, the tines 360 may be positioned in the retracted configuration to avoid inadvertent and/or premature engagement with leaflet tissue or other nearby tissues. The tines 360 may then be moved from the retracted configuration to the expanded configuration just before deploying the proximal elements 316 toward the distal elements 318 to engage the targeted leaflet tissue.

Figure 10A:
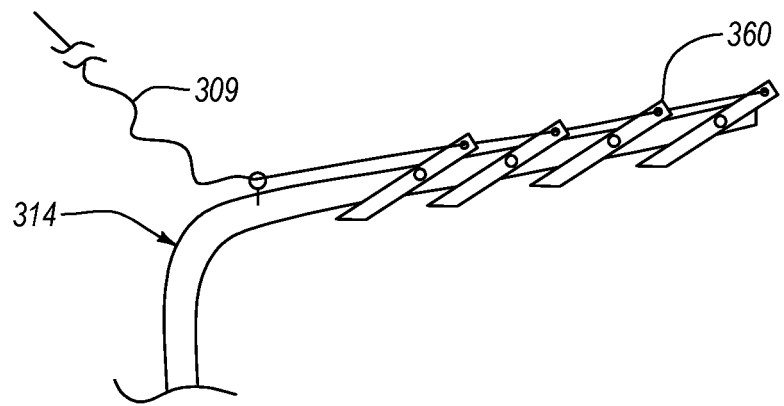
FIGS. 10A to 10C illustrate exemplary mechanisms for adjusting the tines of FIGS. 9A and 9B.
Figure 10B:
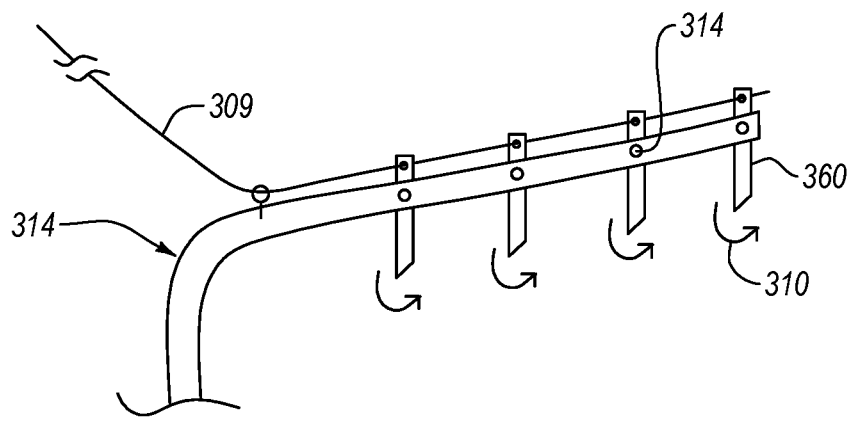
Figure 10C:
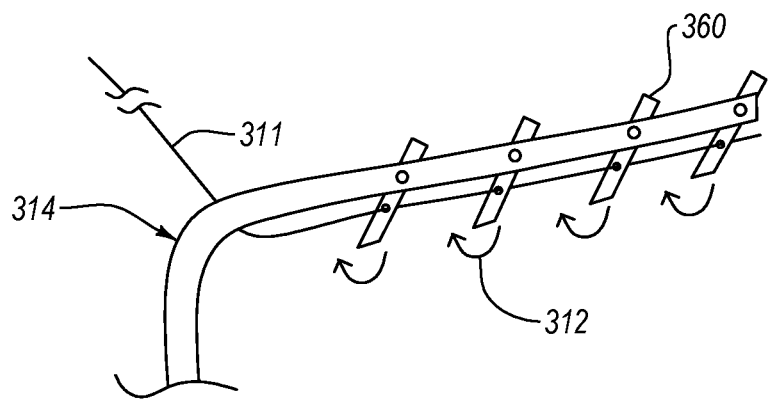

FIGS. 10A to 10C illustrate detailed views of the proximal element 316, showing an exemplary mechanism for enabling adjustment of the tines 360. As shown in FIG. 10A, the tines 360 are in a retracted configuration. A control line 309 is associated with the adjustable tines 360. As shown in FIG. 10B, tensioning the control line 309 causes the tines 360 to rotate outward toward the open configuration, as indicated by arrows 310. The control line 309 may, for example, connect to each of the adjustable tines 360 at a proximal section of each tine, so that tensioning of the control line 309 causes the tines 360 to rotate about respective connection points 314.

In some embodiments, the tines 360 are resiliently biased toward the retracted configuration, such that release of tension in the control line 309 allows the tines 360 to close back toward the retracted configuration. For example, the tines 360 may be formed of a resilient and/or shape-memory material (e.g., nitinol) such that they function as individual leaf springs biased toward a particular configuration. Alternatively, as shown in FIG. 10C, a second control line 311 may be coupled to the tines 360 such that tensioning of the second control line 311 causes the tines 360 to rotate inward toward the retracted configuration, as indicated by arrows 312.

Various alternative embodiments are possible. For example, in some embodiments, the tines 360 may be biased toward the open position, and release of tension in the control line 311 allows the tines 360 to move toward the open configuration.

FIGS. 11A to 11C illustrate exemplary embodiments of a delivery system 400 that may be utilized to deliver one or more of the interventional clip embodiments described herein, such as in one or more of the tricuspid valve repair embodiments described herein. In preferred embodiments, the delivery systems are configured to provide for steering along all three lines of coaptation of a targeted tricuspid valve. The various components of the delivery system function to form the compound curvatures necessary to position an associated interventional clip to the proper orientation relative to the tricuspid valve. As described below, the curvatures may be formed using steerable structures, pre-curved structures, or combinations thereof.

As shown in FIG. 11A, the delivery system includes a handle 408, an guide catheter 402 a sleeve 404 disposed within the guide catheter 402 and configured to be translatable within the guide catheter 402, and a delivery catheter 406 disposed within the sleeve 404 and configured to be translatable within the sleeve 404. The distal end of the delivery catheter 406 is coupled to an interventional clip 414, which may represent any of the interventional clip embodiments described herein. FIG. 11B shows a detailed view of the distal section of the delivery system. The illustrated embodiment also enables easy adjustment in height relative to the tricuspid valve (i.e., superior/inferior positioning) by translating the sleeve 404 within the guide catheter 402 and/or translating the delivery catheter 406 within the sleeve 404.

Manipulation of the guide catheter 402 and/or sleeve 404 enables the interventional clip 414 to be directed through a patient's vasculature to a targeted treatment area of the patient's heart (e.g., the tricuspid valve). Orienting of the guide catheter 402 and/or the sleeve 404 may be achieved using the handle 408. In the illustrated embodiment, for example, various controls 410 (e.g., knobs, levers, switches, dials, other adjustable mechanisms, etc.) are provided for controlling the tensioning of one or more control lines running through at least a portion of the length of the corresponding guide catheter 402 and sleeve 404. Steering may therefore be achieved by adjusting the tension of the one or more control lines to curve the distal end of the guide catheter 402 and/or sleeve 404 in the direction of the applied tension. Additionally, or alternatively, one or more of the guide catheter 402 or the sleeve 404 may be precurved to provide a desired angling for properly traversing a patient's vasculature in the context of a particular procedural approach.

Advancement of the delivery catheter 406 through the sleeve 404 thereby guides the delivery catheter 406 through the resulting curvature, and enables the interventional clip 414 to be delivered to the targeted treatment area in a desired orientation. The clip 414 may then be actuated, deployed, and/or released through manipulation of one or more controls 410 of the handle 408. In some embodiments, a guide catheter can be configured with precurvature and/or steering functionality so as to accommodate transfemoral, transjugular (e.g., inner jugular), trans-apical, or subclavian delivery, or delivery via mini-sternotomy or mini-thoracotomy, with preferred access routes including transfemoral and transjugular approaches.

FIG. 11C illustrates an alternative embodiment in which the sleeve 404 is omitted. In the embodiment illustrated in FIG. 11C, the guide catheter 402 is preferably configured to provide steering for multiple degrees of freedom (e.g., four) for positioning relative to a targeted line of coaptation.

Figure 11D:
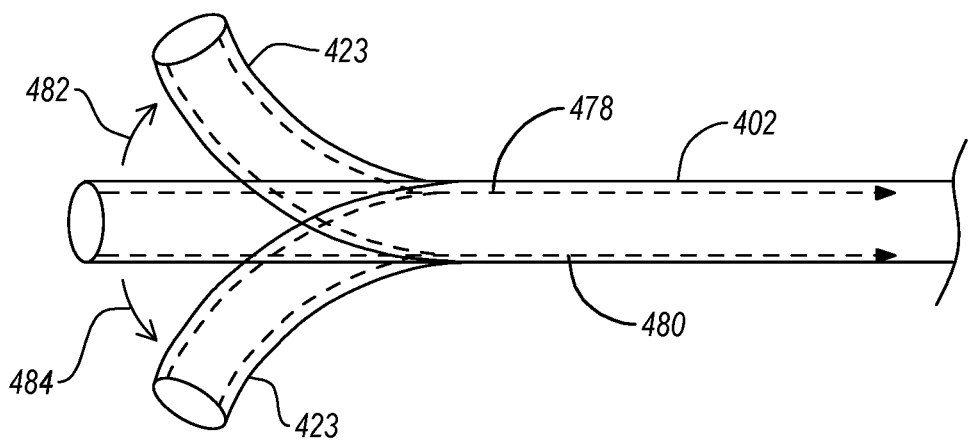

FIG. 11D illustrates an exemplary control line steering mechanism that may be utilized with one or more of the delivery system components described herein. FIG. 11D illustrates a control line steering mechanism associated with the guide catheter 402; however, similar principles may be applied to the sleeve 404 as well. As shown, the guide catheter 402 includes a first control line 478 slidably disposed in a lumen within the wall of the guide catheter 402 and extending to the distal end 423. By applying tension to the control line 478 in the proximal direction, the distal end 423 curves in the direction indicated by arrow 482. Likewise, placement of a second control line 480 along the opposite side of the guide catheter 402 will allow the distal end 423 to be curved in the opposite direction, as indicated by arrow 484. It will be understood that additional control lines may be included at additional sections of the guide catheter 402 to provide additional steering degrees of freedom.

Figure 12:
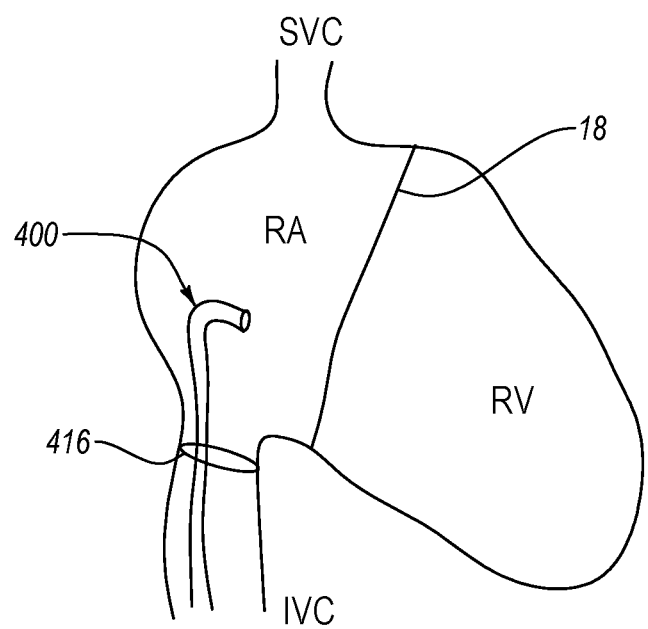
FIG. 12 illustrates a delivery device routed to a heart, showing a support structure deployed to support the position/orientation of the delivery device relative to the targeted cardiac valve.

FIG. 12 illustrates an exemplary embodiment of positioning a delivery system during a tricuspid repair procedure. As shown, the distal end of delivery system 400 is routed to the right atrium ("RA") of the heart to a position superior to the tricuspid valve 18. In this embodiment, the delivery system 400 has been routed to the heart through the inferior vena cava ("IVC") (e.g., through a transfemoral approach). Alternative approaches include access to the right atrium through the superior vena cava ("SVC"), such as through a transjugular approach, or direct access to the right ventricle ("RV"), such as through a trans-apical approach (in which the delivery system 400 would be oriented inferior to the tricuspid valve 18.

As shown, the delivery system 400 includes a support 416 configured to temporarily (e.g., intra-procedurally) anchor the guide system 400 in a desired position within the heart. In the illustrated embodiment, the support 416 is disposed so that, upon deployment, the support 416 abuts against the walls of the inferior vena cava to provide support for the more distal sections of the delivery system 400 within the right atrium and/or to maintain a desired height of the distal end above the valve plane. In a transjugular approach, the support 416 may be configured to engage against the walls of the superior vena cava, for example.

The support 416 may be formed as an expandable wireframe structure (e.g., made from nitinol or other shape-memory material). The wireframe structure may be selectively deployable by unsheathing to expand and deploy and re-sheathing to retract. In other embodiments, the support 416 may be configured as an inflatable structure, such as an inflatable balloon or ring structure. The inflatable structure may be coupled to a control lumen that selectively delivers and withdraws a fluid (e.g., saline or other suitable fluid) to control deployment of the support 416.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a repair device of FIGS. 8A to 9B may be combinable with any element described in relation to any of the delivery systems of FIGS. 11A to 12, any of which may be utilized to perform any of the clip placement procedures illustrated in FIGS. 7A-7D and described in the accompanying description.

EXAMPLES

Mock Loop

A mock loop was used to simulate human circulation. The experimental system consisted of a pulsatile pump connected to a porcine heart obtained from an abattoir. The system accurately replicated the pulse flow and heart valve function in a beating heart. The right heart cardiac output ("CO"), mean pulmonary pressure ($P_{pul}$), and mean diastolic pressure gradient across the tricuspid valve ($\Delta_p$) were obtained from acquired data. Direct visualization of the valvular apparatus was recorded with a fiberscope (Olympus Europe, Hamburg, Germany) inserted in the right atrium. Echocardiographic views of the TV were acquired using an Epiq7 equipped with an X7-2t probe (Philips, Eindhoven, the Netherlands). The mock loop was set to simulate physiological rest conditions (heart rate 60 beats/min; stroke volume 70 ml; $P_{pul}$ 10 to 15 mm Hg). Saline solution was used as working fluid.

FTR Model

Porcine hearts from pigs weighing 170±8 kg were used. The model exploited the tendency of the tricuspid valve ("TV") annulus and right ventricle ("RV") to dilate in order to achieve an experimental model of FTR. In the experimental apparatus, these extremely compliant structures started to dilate at physiological pulmonary pressure values. More specifically, the anterior and posterior portions of the TV annulus dilated, thus pulling the anterior and posterior leaflets away from the septal leaflet. Moreover, due to RV dilation, the papillary muscles anchored to the free ventricular wall were displaced, thus inducing leaflet tethering and in turn further TV incontinence. In the ex vivo model, both of these biomechanical determinants were controlled by means of 2 adjustable bands placed around the heart: 1 around the valvular plane, the other at the level of the papillary muscles. The first band was used to regulate annular diameter; the second to confine and control the RV dilation, thus adjusting papillary muscle displacement and associated leaflet tethering. To obtain physiological TV behavior, the 2 bands were adjusted until experienced surgeons visually verified proper coaptation of the leaflets. CO evaluation, direct fiberscope views, and echocardiographic images were used to support this decision. When the bands were released, coaptation was lost, mean CO consequently decreased, and surgeons qualitatively evaluated the leaflet configuration by intracardiac fiberscope video inspection and echocardiographic imaging.

Implantation Technique

An expert operator implanted devices under fiberscope guidance, using echography as a support imaging technique, allowing for accurate and repeatable clip positioning.

For this study, superior vein access was chosen as direct access to the TV. After inserting the fiberscope in the atrium for direct visual inspection, a J-shaped wire was placed under direct visualization. The steerable guide with its dilator was placed a few centimeters outside the outflow of the superior vena cava to exploit the guide's steerable properties. After removing the dilator, the clip delivery system (MitraClip System, Abbott Vascular, Santa Clara, Calif.) was introduced and oriented in the atrium to obtain a straight and perpendicular trajectory of the clip over the TV plane as required by the experimental protocol. The clip arms were opened at 180 degrees and the TV crossed. Once the leaflets were grasped, the clip was closed and the tension on the system released as instructed by the device manufacturer. After the hemodynamics parameters were recorded, the clip was opened, reverted, and gently pulled back in the right atrium, for a new grasping in a different position. In each heart sample, the clip was deployed only in the position recommended by the protocol.

Experimental Protocol

Twelve hearts obtained from the local abattoir were selected for study. After checking for the absence of anatomic anomalies, the selected hearts were surgically prepared by experienced surgeons to be housed in the mock loop. Three configurations were tested with each heart. First, a physiological, continent TV was obtained, and data were acquired. Second, FTR was simulated via methods discussed earlier. Once data in the pathological configuration were acquired, the treatment of the FTR was performed using the percutaneous mitral valve repair device. In a randomized sequence, the clip was placed between septal and anterior leaflets (S-A), septal and posterior leaflets (S-P), and anterior and posterior leaflets (A-P). For each pair of leaflets, grasping was performed in both the Com and medial (Med) positions. Thus, six total grasping configurations were included for each heart. No clip was deployed in this first sequence of grasping. However, after completing this sequence of grasp and release at the six positions, the clip was finally deployed in 1 of the 6 positions.

Next, the effectiveness of a 2-clip implantation was evaluated. After the first clip was delivered and deployed in 1 of the 6 positions, the second clip was delivered to grasp the remaining 5 positions in each heart.

Endoscopic intracardiac images were acquired before and after each clip grasp procedure to qualitatively assess the pathological model and the percutaneous mitral valve repair treatment effectiveness. Echocardiographic images were used to support these evaluations. Hemodynamic raw data before and after each grasp were sampled and recorded. From the raw data, CO, $P_{pul}$, and mean systolic $\Delta_p$ were averaged over 10 consecutive heart cycles.

Statistical Analysis

Data are presented as mean±SD. To clarify whether the differences among the treatments (A-P, S-P, and S-A in the Med and Com positions) were significant, analysis of variance (ANOVA) for repeated measures was performed. Comparison of the overall data from physiological samples, from Med treatments and from Com treatments compared with the pathological condition, were performed with ANOVA, using Bonferroni correction as a post hoc test.

TABLE 1

Single Clip Treatments

|  | Physiological | Pathological | Post-Treatment Medial | Commissural |
|---|---|---|---|---|
| CO (l/min) | 2.9 ± 0.4 | 2.0 ± 0.4 | 2.6 ± 0.7 | 2.1 ± 0.6 |
| $P_{pul}$ (mm Hg) | 11.0 ± 2.0 | 6.6 ± 2.4 | 9.2 ± 3.8 | 6.9 ± 2.9 |
| $\Delta_p$, mm Hg | 0.1 ± 0.15 | 0.3 ± 0.06 | 0.4 ± 0.5 | 0.4 ± 0.6 |

Considering the Med treatments (MitraClip grasped at mid-leaflet location of both leaflets), TV functionality improved significantly with respect to pathological conditions. Mean CO increased to 2.6±0.7 l/min, and $P_{pul}$ increased to 9.2±3.8 mm Hg (p<0.05 compared with pathological data). Differences between these post-treatment data and physiological condition were not statistically significant, thus indicating a full recovery of initial valve continence. The $\Delta_p$ was 0.4±0.5 mm Hg, with no statistical difference compared with untreated samples.

Conversely, the Com treatments (clip grasped at Com location) did not significantly improve valve continence. Following these treatments, CO was 2.1±0.6 l/min and $P_{pul}$ 6.9±2.9 mm Hg. The $\Delta_p$ did not change significantly (0.4±0.6 mm Hg) after Com treatment either.

Table 2 reports the data grouped by pair of treated leaflets and by grasping position.

TABLE 2

Single-Clip Treatments - Position Specific Data

| Treatment | | CO (l/min) | | | $P_{pul}$ (mm Hg) | | | $\Delta_p$ (mm Hg) | |
|---|---|---|---|---|---|---|---|---|---|
| Position | leaflets | pathological | post-treatment | Δ % | pathological | post-treatment | Δ % | pathological | post-treatment |
| Med | S-P | 2.0 ± 0.5 | 2.9 ± 0.7 | +43% | 7.5 ± 2.6 | 11.3 ± 4.2 | +51% | 0.3 ± 0.4 | 0.5 ± 0.5 |
|  | S-A | 2.0 ± 0.4 | 2.9 ± 0.3 | +41% | 6.7 ± 2.2 | 10.2 ± 2.2 | +53% | 0.3 ± 0.5 | 0.3 ± 0.4 |
|  | A-P | 1.9 ± 0.4 | 1.9 ± 0.4 | −3% | 6.8 ± 2.6 | 6.1 ± 2.5 | −11% | 0.4 ± 0.4 | 0.6 ± 0.5 |
| Com | S-P | 2.0 ± 0.4 | 2.1 ± 0.7 | +1% | 6.3 ± 2.2 | 6.5 ± 2.4 | +4% | 0.4 ± 0.5 | 0.5 ± 0.5 |
|  | S-A | 2.0 ± 0.4 | 2.4 ± 0.7 | +18% | 6.4 ± 2.1 | 8.7 ± 3.7 | +37% | 0.1 ± 0.8 | 0.2 ± 0.8 |
|  | A-P | 2.1 ± 0.4 | 1.9 ± 0.3 | −6% | 5.7 ± 2.5 | 5.5 ± 1.6 | −3% | 0.2 ± 0.5 | 0.5 ± 0.4 |

Differences pre- and post-treatment in the 2-clip implantation treatments were evaluated with the Student t test, with no adjustment for multiple treatments. p Values <0.05 were considered significant. Statistics were evaluated using MiniTab 17 (Minitab, Coventry, United Kingdom).

Results

A total of 144 grasping/deployment procedures in TV were performed. Each grasp was successfully carried out, without issues concerning excessive gaps between leaflets or clip entrapment in the valve chordal apparatus. One of the 12 hearts was discharged following initial grasp attempts due to heart structural failure related to the experimental mock loop.

Table 1 summarizes our overall pooled data obtained with single-clip implantations. Comparing physiological and pre-treatment pathological conditions, the mean CO and the $P_{pul}$ decreased by 31% (from 2.9±0.4 l/min to 2.0±0.4 l/min; p<0.05) and 40% (from 11.0±2 mm Hg to 6.6±2.4 mm Hg; p<0.05), respectively, whereas the $\Delta_p$ did not vary significantly (p=0.363).

Medial treatments involving the septal leaflet allowed the model to achieve a CO and $P_{pul}$ of 2.9±0.7 l/min and 11.3±4.2 mm Hg (S-P Med), and 2.9±0.3 l/min and 10.2±2.2 mm Hg (S-A Med), respectively. Both increments were statistically significant with respect to the pathological conditions, demonstrating recovery of hemodynamics comparable to the physiological model. Regarding Com treatments, S-A Com grasping induced a nonstatistically significant increment in CO (+18%) and in $P_{pul}$ (+37%), whereas S-P Com grasping had no relevant effect on flow rate and pressure. It is noteworthy that the A-P treatments, regardless of Med or Com grasp, induced a slight, even if not statistically significant, worsening of CO and $P_{pul}$ with respect to the pathological conditions. Regarding TV pressure gradients, the maximum recorded value of 0.4±0.5 mmHg was observed in S-A Com tests, with no statistical significance compared with the pre-treatment value, nor clinical relevance.

Figure 13:
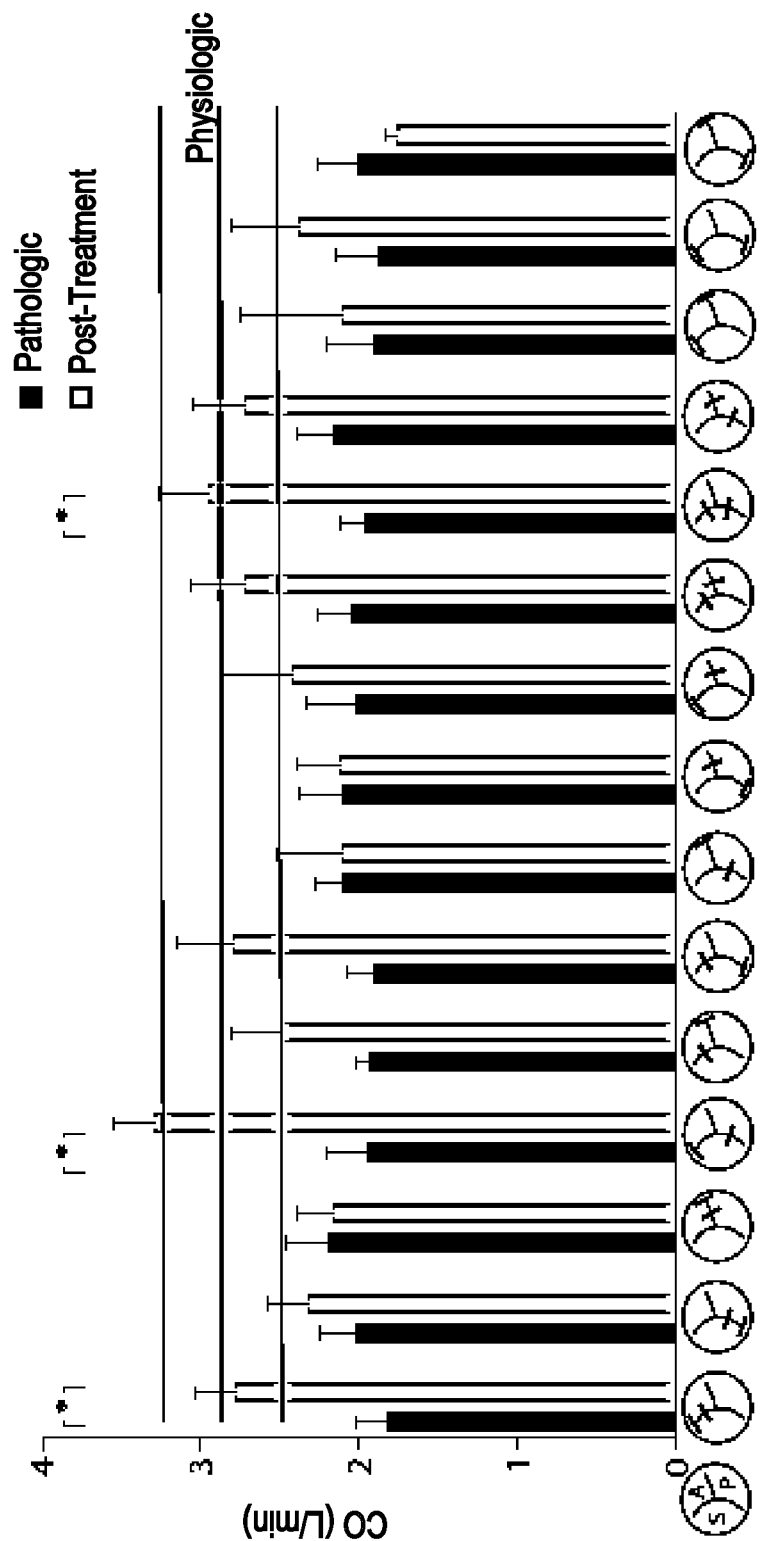
FIG. 13 is a graph showing cardiac output of different heart models following a variety of different FTR treatments.

Table 3 reports numerical data for CO and pressures grouped by leaflet and grasping position for the two-clip implantation procedures. The CO recorded in all the possible positions/leaflet combinations is shown in FIG. 13.

TABLE 3

Two-Clip Treatments

| Treatment | | CO (l/min) | | | $P_{pul}$ (mm Hg) | | | $\Delta_p$ (mm Hg) | |
|---|---|---|---|---|---|---|---|---|---|
| Position | leaflets | pathological | post-treatment | Δ % | pathological | post-treatment | Δ % | pathological | post-treatment |
| Med | S-P + S-A | 2.0 ± 0.3 | 3.0 ± 0.6 | +49% | 7.3 ± 1.3 | 12.1 ± 2.7 | +66% | 0.4 ± 0.3 | 0.8 ± 0.6 |
|  | A-P + S-A | 2.0 ± 0.4 | 2.7 ± 0.7 | +33% | 8.1 ± 1.1 | 19.8 ± 6 | +21% | 0.1 ± 0.1 | 0.5 ± 0.2 |
|  | A-P + S-P | 2.2 ± 0.4 | 2.7 ± 0.7 | +25% | 7.4 ± 1.0 | 7.4 ± 4.6 | 0% | 0.3 ± 0.3 | 1.2 ± 0.8 |
| Com | S-P + S-A | 1.9 ± 0.4 | 2.4 ± 0.9 | +27% | 6.2 ± 2.4 | 7.0 ± 4.9 | +12% | 0.2 ± 0.2 | 0.3 ± 0.3 |
|  | A-P + S-A | 1.9 ± 0.4 | 2.1 ± 1.1 | +11% | 4.7 ± 2.2 | 6.6 ± 5.0 | +40% | 0.2 ± 0.3 | 0.4 ± 0.1 |
|  | A-P + S-P | 2.0 ± 0.5 | 1.8 ± 0.1 | −12% | 5.1 ± 3.7 | 5.1 ± 0.3 | 0% | 0.4 ± 0.1 | 0.3 ± 0.1 |
| Med + Com | S-P | 2.0 ± 0.4 | 2.3 ± 0.5 | +15% | 6.6 ± 2.3 | 4.5 ± 3.9 | −32% | 0.7 ± 0.6 | 0.9 ± 0.7 |
|  | S-A | 1.8 ± 0.5 | 2.8 ± 0.6 | +52% | 6.9 ± 2.0 | 7.9 ± 1.4 | +14% | 0.1 ± 0.2 | 0.3 ± 0.2 |
|  | A-P | 2.2 ± 0.5 | 2.2 ± 0.5 | 0% | 6.3 ± 3.4 | 6.4 ± 0.3 | +2% | 0.3 ± 0.3 | 0.4 ± 0.2 |

Medial treatment, regardless of the leaflet pair treated, induced an increment with respect to pathological conditions in both CO (+35%; p<0.05) and $P_{pul}$, ($P_{pul}$+29%; p=0.13). Commissural treatments induced negligible and nonsignificant increments in CO and $P_{pul}$ (+10% and +16%, respectively; p>0.52), whereas the pooled CO increment was slightly more relevant (+22%; p=0.9) following a zipping procedure (i.e., the Med and Com grasping between the same couple of leaflets).

Data showed varying trends dependent on the location of the first clip. In heart samples in which the first clip deployment was in a Med position, CO increased from 2.1±0.4 l/min (pathological) to 2.4±0.4 l/min (post first procedure; p<0.05), and remained stable post second procedure (2.4±0.5 l/min; p=0.611). In heart samples, in which the first clip deployment was performed in Com positions, CO was stable post first procedure (from 1.8±0.5 l/min to 1.8±0.3 l/min; p=0.635), and increased to 2.5±0.7 l/min post second Med procedure (p<0.05 with respect to first).

Two-clip data confirmed that treatments involving the septal leaflet in Med positions induced an increase of both CO and Ppul. The most relevant increase in CO was recorded post 2-clip implantation in the S-A Com position and S-P Med position (+69% with respect to pathological data; p<0.05) (see FIG. 13). CO also increased when clips were implanted between S-A Med and S-P Med (+49%; p<0.05) and with implantation of both clips along the S-A line of coaptation (+52%; p<0.05). After each of these treatment conditions, physiological-like CO and $P_{pul}$ were restored. It is noteworthy to add that when the 2 clips were implanted in Med and Com positions in S-P, the hemodynamics did not improve significantly. This could be due to a detrimental effect of Com implantation in S-P. The worst recorded TV function was recorded post-implantation of the clips in A-P Com and S-P Com positions (=12% of CO; p=NS with respect to pathological). Two-clip implantations did not induce a clinically relevant increase of the TV $\Delta_p$ in any of the treatment configurations (maximum $\Delta_p$ was 1.4±0.7 mm Hg, recorded post A-P Com and S-P Med treatment).

The anterior and posterior segments of the TV annulus correspond to the free wall of the ventricle. When dilation occurs, the anterior and posterior segments of the annulus move away from the relatively fixed septal segment and elicit the loss of coaptation. Therefore, treatments involving the septal leaflet and 1 of the other 2 (anterior or posterior) leaflets are expected to reduce the gap between the free margin of the leaflets and improve leaflet coaptation. Study results confirmed these inferences. Grasping procedures that involved the septal leaflet achieved better post-procedural results in terms of cardiac output and pressure recovery.

Conversely, A-P 1-clip grasping consistently induced a decrease in CO. The major effect of a clipping procedure in the A-P location is a reduction of the leaflet-gap area between A and P leaflets because the 2 leaflets are forced closer to each other by the clip. This procedure has no relevant effect on the shift of the A-P portion of the annulus with respect to the septal leaflet. There was no mechanical constraint to force the free and dilated A-P portion of the annulus to stay closer to the septal portion. Moreover, one can speculate that this procedure induced a reciprocal tethering of the A and P leaflets, causing their free margins to be pulled further away from the septal leaflet, thus worsening valve performance.

A statistically significant increment in TV continence was associated with Med grasping. In particular, 1-clip Med grasps between S-A or S-P leaflets induced noteworthy and statistically significant increases in cardiac output and mean pulmonary pressure. Simulated physiological-like conditions were restored following these treatments.

Conversely, the Com grasping was almost ineffective, if not detrimental. The only exception was the Com grasping between septal and anterior leaflets, which led to an increment of 18% of the CO. A-P leaflet grasping at the commissure induced a worsening of the valve continence, and this was even more evident with respect to Med grasping.

The so-called "zipping procedure" (i.e., the grasping of the Com and Med position of the same pair of leaflets) was particularly effective when applied between S-A leaflets, with a full recovery of physiological-like simulated hemodynamics, but ineffective between anterior and posterior. This confirmed the results of the 1-clip procedure: S-A procedures, regardless of clip positioning, were more effective in terms of functional recovery of the modeled FTR.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. An interventional tissue clip device configured for repair of a cardiac valve, the clip device comprising:
   a pair of distal elements rotatably joined to a coupling member; and
   a pair of proximal elements resiliently biased toward the pair of distal elements, the pair of distal elements being configured to receive the pair of proximal elements so as to enable the grasping of tissue therebetween, the pair of proximal elements including a plurality of adjustable tines moveable between a retracted configuration and an open configuration, the open configuration positioning the tines more perpendicular to respective longitudinal axes of the pair of proximal elements so as to enable enhanced grasping of tissue by the pair of proximal elements;

wherein the tines are coupled to one or more control lines, wherein adjusting tension of the one or more control lines controls movement of the tines between the open and retracted configurations.

2. The device of claim 1, wherein the tines are configured to project more inwardly when in the retracted configuration relative to when in the open configuration.

3. The device of claim 1, wherein the tines are biased toward the retracted configuration and the one or more control lines includes a proximal control line, and wherein application of tension to the proximal control line positioned on a proximal side of proximal element of the pair of proximal elements moves the tines toward the open configuration.

4. The device of claim 3, wherein the one or more control lines includes a distal control line positioned on a distal side of proximal element of the pair of proximal elements, and wherein application of tension to the distal control line moves the tines toward the retracted configuration.

5. The device of claim 1, wherein the tines are biased toward the open configuration and the one or more control lines includes a distal control line, and wherein release of tension on the distal control line positioned on a distal side of each proximal element of the pair of proximal elements allows the tines to move to the open configuration.

6. The device of claim 1, wherein each proximal element of the pair of proximal elements has a length greater than 10 mm.

* * * * *